United States Patent [19]

Esders et al.

[11] 4,166,763
[45] Sep. 4, 1979

[54] ANALYSIS OF LACTIC ACID OR LACTATE USING LACTATE OXIDASE

[75] Inventors: Theordore W. Esders, Webster; Charles T. Goodhue, Rochester; Richard M. Schubert, Spencerport, all of N.Y.

[73] Assignee: Eastman Kodak Company, Rochester, N.Y.

[21] Appl. No.: 749,546

[22] Filed: Dec. 10, 1976

[51] Int. Cl.$^2$ .................. C07G 7/02; G01N 31/14
[52] U.S. Cl. ........................ 435/28; 435/189; 435/805; 435/885
[58] Field of Search ............... 195/99, 103.5 R, 63, 195/68, 62

[56] References Cited

U.S. PATENT DOCUMENTS 3,907,642  9/1975   Richmond ............... 195/103.5 R
3,992,158  11/1976  Przybylowicz et al. ... 195/103.5 R

OTHER PUBLICATIONS

Barman, Enzyme Handbook, vol. 1, Spring-Verlag New York, Inc. 1969, p. 111.
Eichel et al., J. Biol. Chem., vol. 237, No. 3, 1962, pp. 940–945.
London, J. Bact., vol. 95, No. 4, 1968, pp. 1380–1387.
Sutton, J. Biol. Chem., vol. 226, 1957, pp. 395–405.
Dixon et al., Enzyme, Academic Press Inc., Publishers, New York (1964), pp. 680 & 681.

Primary Examiner—David M. Naff
Attorney, Agent, or Firm—Ronald P. Hilst

[57] ABSTRACT

Compositons and multilayer analytical elements comprising lactate oxidase which is substantially free of catalase and preferably produced by *Streptococcus faecalis* ATCC 12755 are provided for the quantitative analysis of lactic acid or lactate, especially in serum. The lactate oxidase catalyzes the reduction of lactic acid or lactate to pyruvate and hydrogen peroxide and the quantity of lactic acid or lactate is determined by detecting the amount of hydrogen peroxide produced. Preferably, the hydrogen peroxide is detected colorimetrically using a peroxidase-catalyzed detection system.

27 Claims, 5 Drawing Figures

- SPREADING LAYER
- SUBBING LAYER
- GEL PAD
- REAGENT LAYER
- SUPPORT

ANALYSIS OF LACTIC ACID OR LACTATE USING LACTATE OXIDASE

FIELD OF THE INVENTION

This invention relates to compositions and methods for clinical analysis of lactic acid and in particular to the quantitative determination of lactic acid based on a lactate oxidase-$H_2O_2$ detection scheme.

DISCUSSION OF PRIOR ART

The level of lactic acid in the blood is a general indicator of the adequacy of blood circulation and is the best biochemical criterion of the severity of circulatory failure in which increased lactate levels are observed. It is the single best laboratory measurement for the general assessment of the prognosis in critically ill patients. Also lactate and pyruvate levels increase rapidly in normal individuals following administration of glucose or injection of insulin. This rise is delayed or absent in diabetes mellitus. So determinations of both lactate and glucose concentrations could distinguish between pancreatic diabetes and other disorders exhibiting decreased glucose tolerance. Currently lactic acid is quantitated enzymatically via the lactate dehydrogenase (LDH) reaction. This is a nucleotide-linked method in which reduced nicotinamide adenine dinucleotide (NADH) formation is measured either by absorbance or fluorescence. The equilibrium of the reaction, however, favors formation, not utilization, of lactic acid. Oxidation of lactate to pyruvate (with concommitant NADH formation) is favored only at pH values higher than pH 8.0 and in the presence of carbonyl trapping agents. These, of course, are limitations of the method in addition to the general problems of making ultraviolet or fluorescence measurements and the instability of both lactate dehydrogenase and the nucleotide cofactor.

Various methods of analyzing for lactic acid using LDH are described in "Methods of Enzymatic Analysis," 2nd English ed., H. U. Bergmeyer, Ed., Academic Press, Inc., New York and London (1970) in articles beginning at pages 1472, 1475, 1483 and 1492. At page 1483, Wieland et al describes a colorimetric method for determining lactate in serum employing yeast lactate dehydrogenase and potassium hexacyanoferrate (III). Interferences from ascorbic acid, glutathione, cysteine and NADH, all of which reduce the hexacyanoferrate are encountered. The determination of lactic acid using NAD+ and LDH is described by Gawehn et al, p. 1492, and by Noll, p. 1475. A method for lactic acid determination using 3-acetylpyridine-adenine dinucleotide (APAD) instead of NAD+ is described by Maurer et al at p. 1472. For this method reagents must be freshly prepared and the determinations are read in the UV region of the spectrum. All of the above methods have a further disadvantage in that deproteinization of the blood sample is required. Drawbacks of the known LDH reference methods for determining lactic acid are discussed generally by Young et al in *Clinical Chemistry*, Vol. 18, p. 1041 (1972).

SUMMARY OF THE INVENTION

The present invention takes a different approach to the determination of lactic acid and provides compositions and methods for such determinations using lactate oxidase. In accord with the present invention, a sample of fluid containing lactic acid or a lactate reacts in the presence of lactate oxidase and oxygen to produce pyruvate and hydrogen peroxide. The hydrogen peroxide is then detected to determine the amount of lactate present in the sample. In a preferred embodiment of the invention, the hydrogen peroxide is detected by oxidation of a chromogen in the presence of peroxidase.

In accordance with the invention, a composition for the detection of lactic acid or lactate in a sample of a fluid comprises a lactate oxidase preparation that in the presence of oxygen will convert lactic acid or lactate to pyruvate and detectable hydrogen peroxide. Preferably the lactate oxidase preparation is substantially catalase-free. As used herein, the term "substantially catalase-free" means that there is no detectable catalase present or that there are small amounts of catalase present that are insufficient to affect the accuracy and reproducibility of the assay.

DETAILED DESCRIPTION OF THE INVENTION

Figure 1:
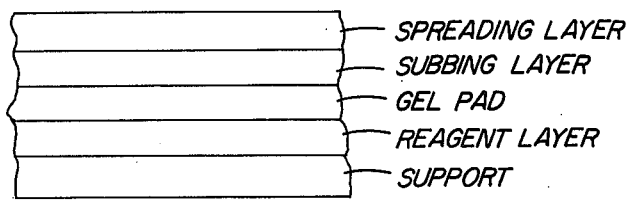

According to the invention, a lactate oxidase capable of catalyzing the conversion of lactic acid or lactate to pyruvate and hydrogen peroxide in the presence of oxygen is used to quantitatively determine lactic acid or lactate. Various lactate oxidases have been reported. Generally, however, the lactate oxidases reported do not catalyze a reaction producing hydrogen peroxide. Examples of such lactate oxidases are reported by Sutton in *Journal of Biological Chemistry*, Vol. 226, p. 395 (1957) and by London in *Journal of Bacteriology*, Vol. 95, No. 4, p. 1380 (1968). Enzyme Handbook, Vol. 1, by Thomas E. Barman, Springer-Varlag New York, Inc. (1969) describes a lactate oxidase derived from *Mycobacterium phlei* that allegedly catalyzes the oxidation of L-lactate producing hydrogen peroxide. Checking the references cited by Barman shows that the reaction equation indicating the production of hydrogen peroxide is in error and should indicate instead that water is produced.

To our knowledge, the only reported source of a lactate oxidase that allegedly converts lactate to pyruvate and hydrogen peroxide is that published by Eichel et al, "Respiratory Enzyme Studies in *Tetrahymena pyriformis*," *Journal of Biological Chemistry*, Vol. 237, No. 3, p. 940 (1962). Because of the catalase activity reported in the lactate oxidase preparation obtained from *Tetrahymena pyriformis*, it would not be suitable for use in an assay, especially one based on the detection of hydrogen peroxide (catalase decompose hydrogen peroxide and thus is a potential source of error). Other disadvantages of the lactate oxidase from Tetrahymena include its partial solubility (only 4 to 57% of the enzyme was reported as soluble), its instability (43 to 60% of activity was reported to be lost after storage or dialysis at 2° C. for 24 hours), and a relatively low specific activity (a specific activity of approximately 0.02 μmole lactate per minute per mg protein was calculated based on $Q_{92}$ (N)=162).

We have discovered that a lactate oxidase which can convert lactate to pyruvate and hydrogen peroxide is produced by *Streptococcus faecalis* ATCC 12755. This lactate oxidase from *S. faecalis* is highly specific for L-lactate having a $K_m$ of about 0.2 mM for lactate. This lactate oxidase is also soluble, catalase-free, highly stable when compared to that from Tetrahymena, and has a specific activity of at least about 0.1 μmoles lactate per minute per mg protein. The lactate oxidase from *S. faecalis* has been found stable to dialysis and $(NH_4)_2$ $SO_4$ fractionation, and has been found stable for at least 3 months when stored at $-20°$ C.

When a sample containing an unknown quantity of lactic acid or lactate is assayed using a composition of this invention containing lactate oxidase, hydrogen peroxide is produced in proportion to the quantity of lactic acid or lactate in the sample. The hydrogen peroxide is detected by any known method and the unknown quantity of lactic acid or lactate is determined using a calibration curve obtained by assaying samples having known quantities of lactic acid or lactate.

Known methods for detecting and/or quantifying hydrogen peroxide in assays such as described in the present invention generally use a composition containing a substance having peroxidative activity, e.g., peroxidase and peroxidase-like substances, and material which undergoes a detectable change (generally a visible change) in the presence of hydrogen peroxide and the peroxidative substance. A complete list of the prior art which describes such compositions is too extensive for presentation here. However, a few representative patents which describe such materials are: U.S. Pat. Nos. 2,912,309; 2,981,606; 3,349,006; 3,092,465; 3,558,435; 3,595,755; 3,627,697; 3,627,698; 3,630,847; 3,654,179; 3,654,180; and 3,853,470. Examples of various color forming substrates of peroxidase and peroxidase-like substances which have been suggested in the prior art include, among others, the following substances with a coupler where necessary:

(1) Monoamines, such as aniline and its derivatives ortho-toluidine, para-toluidine, etc.;

(2) Diamines, such as ortho-phenylenediamine, N,N'-dimethyl-para-phenylenediamine, N,N'-diethyl phenylenediamine, benzidine (which produces a blue or brown color), dianisidine (turns green or brown), etc.;

(3) Phenols, such as phenol per se (producing a yellow color), thymol, ortho-, meta-, and para-cresols (producing a green-yellow color, a pink color and a milky suspension, respectively), alpha-naphthol (producing a magenta color), beta-naphthol (producing a white precipitate), etc.;

(4) Polyphenols, such as catechol, guaiacol (which forms an orange color), orcinol, pyrogallol (producing a reddish or yellow color), p,p-dihydroxydiphenyl and phloroglycinol;

(5) Aromatic acids, such as salicyclic, pyrocatechuic and gallic acids;

(6) Leuco dyes, such as leucomalachite green (to produce malachite green) and leucophenolphthalein (desirably employed in an alkaline medium);

(7) Colored dyes, such as 2,6-dichlorophenolindophenol;

(8) Various biological substances, such as epinephrine, the flavones, tyrosine, dihydroxyphenylalanine (producing an orange-reddish color) and tryptophane;

(9) Other substances, such as gum guaiac, guaiaconic acid, potassium, sodium, and other water soluble iodides; and bilirubin (producing a greenish color); and

(10) Such particular dyes as 2,2'-azine-di(3-ethylbenzothiazoline-(6)-sulfonic acid) and 3,3'-diaminobenzidine.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms and may be produced by fermentation. Certain synthetic peroxidases, such as those disclosed by Theorell and Maehly in Acta Chem. Scand., Vol. 4, pages 422–434 (1950), are also satisfactory for use in $H_2O_2$ detection systems. Less satisfactory are such substances as hemin, methemoglobin, oxyhemoglobin, hemoglobin, hemochromogen, alkaline hematin, hemin derivatives and certain other compounds which demonstrate peroxidative or peroxidase-like activity, namely, the ability to catalyze the oxidation of another substance by means of hydrogen peroxide and other peroxides.

Other substances which are not enzymes but which demonstrate peroxidative activity are: iron sulfocyanate, iron tannate, ferrous ferrocyanide, chromic salts (such as potassium chromic sulfate) absorbed in silica gel, etc.

The compositions and methods for detecting lactic acid and lactates described in the present invention are useful in conventional liquid assays. It should be readily apparent to the skilled artisan that all of the reagents may be provided in dry or lyophilized form and reconstituted with water immediately prior to use. Compositions of this type are clearly contemplated by this invention.

The assay compositions described herein may, of course, be incorporated into a matrix of absorbent material of the type well known in the art by impregnation or otherwise to yield test compositions suitable for qualitative or semi-quantitative assay of lactic acid or lactates. Typical such materials and elements produced therewith which can be adapted for the assay of lactic acid or lactates are those described, for example, in the following U.S. Pat. Nos. 3,092,465; 3,418,099; 3,418,083; 2,893,843; 2,893,844; 2,912,309; 3,008,879, 3,802,842; 3,798,064; 3,298,739; 3,915,647; 3,917,453; 3,933,594; 3,936,357; etc.

In addition, the compositions and methods described in the present invention are particularly useful when the analyte determination is performed in a multilayer element of the type described in U.S. Pat. No. 3,992,158, issued Nov. 16, 1976, in the names of Przybylowicz and Millikan, the disclosure of which is hereby incorporated by reference. Elements of this type generally comprise:

(1) a spreading layer;
(2) a reagent layer that is in fluid contact with the spreading layer under the conditions of use; and
(3) optionally, a support.

Preferred elements of this type employ a non-fibrous spreading layer.

Multilayer elements useful in the practice of this invention may also include registration layers, i.e. layers which underlie spreading and reagent layers, contain no interactive materials and serve only to receive dyes produced in the overlying layers. Such layers generally comprise a matrix permeable to the dye and as desired other adjuvants such as mordants, surfactants etc. which enhance layers and their arrangement in analytical elements are described in more detail in Belgian Pat. No. 831,660 published Jan. 23, 1976 in the name of P. Clement and entitled "Integral Element for Analysis of Liquids."

The choice of a matrix material for the reagent or registration layers described herein is, of course, variable and dependent on the intended method of use of the element as well as the particular interactive materials which are incorporated therein as described hereinafter. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use parameters for any particular element. To enhance permeability of the reagent layer, if not porous, it is often useful to use a matrix material that is moderately swellable in the solvent or dispersion medium of liquid under analysis.

In addition to its permeability, the reagent layer is desirably substantially free from any characteristic that might appear as or contribute to mottle or other noise in the detection of an analytical result produced in the integral element. For example, variations in color or in texture within the reagent layer (as may occur in fibrous materials such as when papers are used as a permeable medium) may be disadvantageous due to non-uniform reflectance or transmittance of detecting energy, e.g., when the detectable change has occurred in and is detected in the reagent layer. Also, although fibrous materials like filter and other papers are highly permeable overall, they typically exhibit widely ranging degrees of permeability between regions of the paper, for example, based on structural variations such as fiber dimensions and spacing. As a result, such materials are not considered uniformly permeable and, as such, are not preferred in reagent layers and other layers of the present invention which preferably comprise non-fibrous material.

Supports: The integral analytical elements can be self-supporting or the spreading layer, reagent layer and any other associated layers can be coated on a support. Useful support materials, when such are used, include paper and polyolefin coated paper, as well as a variety of polymeric materials such as cellulose acetate, poly(ethylene terephthalate), polycarbonates and polyvinyl compounds such as polystyrenes, etc. The support can be opaque or it can transmit light or other energy depending, of course, on the mode of detection used. A support of choice in any case will be compatible with the intended mode of result detection. Preferred supports include transparent support materials capable of transmitting electromagnetic radiation of a wavelength within the region between about 200 nm and about 900 nm. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer is interposed in the element between the support and the spreading layer. Specifically preferred transmission ranges for elements of the present invention will be apparent from the discussion of the various preferred indicator compositions discussed above. When used, supports having thicknesses of between about 1 and about 10 mils have been found satisfactory, although the thickness can vary broadly depending on such factors, for example, as the intensity of the detecting radiation and the sensitivity of the detecting apparatus.

Other Layers: The analytical element of the present invention is preferably adapted for use in an analytical system employing reflection techniques of spectrometric analysis, and consequently generally includes a layer which functions as a reflecting layer and thereby provides a suitable background for spectrophotometric measurement of colorimetric or other indicator reactions through the support side of the element. The reflecting layer will permit the passage of analyte to the reagent or registration layer and should provide an effective background for reflection spectrophotometry. A white background is generally preferred for this purpose. In view of its function as a background for indicator formed in the reagent or registration layer, any reflective layer will normally intervene the spreading and reagent or registration layers. Such a layer may, however, intervene a reagent and registration layer where such structure is appropriate. Reflectance can be provided by a layer also serving, for example, as a spreading layer or it can be provided by an additional layer that may not have an additional function with the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Filtering layers may also be present in the element. The composition and preparation of such layers are well known in the art and, when present, they serve to remove from the sample components which could interfere with the indicating reaction or otherwise hinder quantification. Thus, in the use of the multilayer analytical element for analysis of lactic acid in whole blood, a separate filtering layer could serve to remove red blood cells while transmitting the serum to the layer below. In the analysis of blood serum or other fluids, the filtering layer may serve to remove unwanted components which could hinder or confuse the primary indicating reaction. Alternatively, the aforementioned blush polymer layers may also serve as filtering layers. If the element is to be used for analysis of whole blood, it is desirable that any filtering layer have a pore size of 0.5 to 5 microns.

In order to increase adhesion of the reagent layer to the superimposed spreading, filtering, and reflective layer(s) it has been found advantageous in some cases to apply a permeable separating or interlayer which serves as a subbing layer to improve adhesion between such layers. So long as the interlayer is sufficiently permeable to permit the analyte to reach the reagent layer, does not inhibit any reagents in adjacent layers, and provides the adhesion improvement desired, it may be formed of almost any material. Such materials are well known to those skilled in the art.

Among the interlayer materials which have provided particularly advantageous results are polymeric film forming materials such as poly(n-vinyl-2-pyrrolidone), poly(n-isopropylacrylamide), copoly(vinyl acetate/vinyl neodecanoate) (20 wt. percent vinyl acetate), and copoly(vinyl neodecanoate/n-vinyl-2-pyrrolidone) (10 and 30 wt. percent vinyl neodecanoate).

Since it is critical that the permeability of the interlayer be maintained, these layers are necessarily very thin and may generally range in thickness from monolayers of materials on up to layers on the order of 1 mil. When polymeric interlayers of the materials mentioned above are used, these are generally applied at levels ranging from about 90 mg/m$^2$ to about 1000 mg/m$^2$ depending on such properties as the density of the polymer, the permeability of the ultimate subbing layer, etc.

Surface treatments which improve adhesion between layers, for example, electron bombardment, etc. may also be desirable.

Element Preparation: In preparing integral analytical elements of this invention, the layers can be preformed as separate layers and thereafter laminated or maintained as separate layers until brought into fluid contact when the element is used. Layers prepared as separate members are typically coated from solution or dispersion on a surface from which the layer can be physically stripped when dried. However, a convenient procedure which can avoid the necessity for multiple stripping and lamination steps when contiguous layers are desired is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. Interlayer adhesion problems can be overcome without harmful effect by means of surface treatments including extremely thin application(s) of subbing materials such as are used in photographic films.

In some embodiments, certain of the reagent materials may be incorporated into the spreading layer. For example, the enzyme lactate oxidase can be incorporated into this layer to obtain hydrogen peroxide production before the sample reaches the reagent layer containing the materials which act upon the H$_2$O$_2$ to produce a detectable change.

According to one embodiment wherein the spreading layer performs the functions of filtering and spreading, the layer is advantageously prepared by simultaneously coating two strata of a binder such as cellulose acetate dissolved in a mixed organic solvent to provide "blush" polymer layers as described in Przybylowicz and Millikan, supra. Such a technique simplifies the manufacturing operation by reducing the multiple coating of multiple layers to a single multiple coating operation while providing a highly useful spreading and/or filtering layer. Optionally, if desired, either or both of the discrete layers may contain dispersed therein a reflective pigment such as TiO$_2$.

Equipment and techniques suitable for simultaneous coating of various individual layers within either the spreading layer of the reagent layer are described in U.S. Pat. No. 2,932,855 issued Apr. 19, 1960.

The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers having a thickness of from about 50 microns to about 300 microns have been particularly useful, although wider variations in thickness are acceptable and may be desirable for particular elements.

When preparing an isotropically porous spreading layer, it is useful to have a void volume comprising at least about 25% of the total layer volume, and void volume of from 50–95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous "blush" polymers are used in the spreading layer. The void volume of any such layer can be calculated with reasonable accuracy by a variety of techniques such as the statistical method described in Chalkley, *Journal of the National Cancer Institute*, 4, 47 (1943) and by direct weighing and determining the ratio of actual weight of the layer to the weight of solid material equal in volume to that of the layer comparably composed of constituents from the layer.

For reagent layers, a coating solution or dispersion including the matrix and incorporated interactive materials can be prepared, coating as discussed herein, and dried to form a dimensionally stable layer. The thickness of any reagent layer and its degree of permeability are widely variable and depend on actual usage. Dry thicknesses of from about 10 microns to about 100 microns have been useful.

Furthermore, the element may incorporate several discrete reagent layers, each of which performs a specific operation in the analytical procedure. In one embodiment, the reagent system for the determination of lactic acid may be coated in two discrete layers. The uppermost of these layers can contain the reagents necessary for hydrogen peroxide generation from lactic acid and the second could contain the color or other indicator system.

In an analytical element for the assay of lactic acid the enzyme lactate oxidase is incorporated in either the spreading or reagent layer at coverages of about 50 to 500 U/m$^2$ and preferably at coverages of about 150 to 350 U/m$^2$. Peroxidase is advantageously employed in such an element at coverages of about 2000 to 20,000 U/m$^2$ and preferably at coverages of about 3,000 to 10,000 U/m$^2$ depending upon the type of indicator system being used. However, in particular circumstances higher or lower coverages of peroxidase may be useful. One skilled in the art can easily determine the proper level for any particular use.

In a preferred embodiment, the layers described herein are formed by coating from solutions or dispersions, for example, as described in the aforementioned Przybylowicz and Millikan application. For coating purposes, it is often necessary to include coating aids which impart appropriate coating properties to the layers.

Whatever coating aids are used for this purpose, or those described below, it is important that they do not inhibit the activity of lactate oxidase or any of the other reagents present in any of the various reagent layers. Particularly useful coating aids for this purpose include nonionic surfactants such as the octyl phenoxy polyethoxy ethanols commercially available from Rohm and Haas Co. under the Triton tradename (X-100, 102, 165, 305, and 405 being particularly useful), (p-nonylphenoxy) glycerol commercially available from Olin Mathieson Corp. under the tradename Surfactant 10G, and the carbowax polyethylene glycols 600, 1540, 4000, 6000 and 20 M available from Union Carbide, the oleyl ether of Carbowax 1540 being particularly useful. Other useful coating aids are glycerine and Alkanol XC (triisopropyl naphthalene sulfonate, sodium salt) commercially available from Dupont.

Surfactant levels on the order of from about 0.5 to about 4.0 g/m$^2$ in the reagent layer and from about 1.0 to about 5.0 g/m$^2$ in the spreading layer have generally been found to produce no or minimal inhibitory effects while providing improved coating and sample spreading characteristics.

Hardeners can be used in layer preparation to insure proper and rapid set of the vehicle, to prevent damage on handling and to inhibit undesirable intermixing of adjacent layers. Their use is well known in the art and well documented and hence no further discussion is presented herein. Whatever organic or inorganic hardeners are used for this purpose, it is important that they do not adversely affect any of the other reagents present in the layers to any great degree. Hardeners which have been found particularly useful for this purpose include glutaraldehyde and bis(vinylsulfonylmethyl)ether.

Use of the Element: Thus, in use, as demonstrated by the lactate determination examples which follow, a drop size sample on the order of from about 5 to about 50 μl is applied to the spreading or other outermost layer using known drop application techniques. In passage through the spreading layer the sample drop is spread so that a metered amount thereof is delivered to the underlying reagent layer wherein the degradation of the lactate and production of hydrogen peroxide occur.

Alternatively, depending on the embodiment used, the production of the hydrogen peroxide may occur in the spreading layer or an upper reagent layer, and the hydrogen peroxide delivered to the underlying reagent layer. In either case, the hydrogen peroxide is quantitated in a reagent layer using the indicator system of choice and known techniques, and the concentration of total lactate present in the applied sample determined.

In a particular embodiment of the present invention, a multilayer element illustrated by FIG. 1 is adapted for the assay of lactic acid or lactate in serum. The presently preferred element comprises four layers coated on a support. The first layer is the reagent layer and in this embodiment, contains all of the reagents necessary to degrade lactic acid or lactate and to detect the amount of hydrogen peroxide thus produced. The second layer is a gel pad comprising deionized gelatin which is used in this embodiment to prevent the chromogen of choice (an organic solvent soluble leuco dye) from migrating into the spreading layer during the coating thereof in the manufacture of the element. The third layer is a sub layer to promote adhesion between the gel pad and the fourth layer which is the spreading layer.

The following examples are included to further illustrate the present invention. Unless otherwise indicated the following procedures apply to the examples.

1. Preparation of Lactate Oxidase a. Culturing of *Streptococcus faecalis*: *Streptococcus faecalis* was grown in a medium containing yeast extract, glucose, tryptone, K$_2$HPO$_4$, metal salts and vitamins. The cells were harvested in mid-log phase, collected by centrifugation, washed once with potassium phosphate buffer, pH 7.0, and stored frozen until used.

b. Extraction and purification of lactate oxidase: *S. faecalis* cells (260 g wet weight) were thawed at 5° C. for about 65 hours. Cells were suspended in a total volume of 1 liter of 0.1 M potassium phosphate buffer, pH 7.0 and blended to homogeneity in a Waring blender for 2 minutes. The cell suspension was centrifuged for 20 minutes at 13,000×g and the pellet containing cell debris was discarded. These and all remaining procedures were carried out at 5°.

A one-percent protamine sulfate solution was added slowly with stirring over a period of one hour to bring the crude cell-free extract to 0.05 percent protamine sulfate. The extract was then centrifuged at 13,000×g for 20 minutes and the pellet containing precipitated nucleic acids was discarded.

Solid enzyme grade (NH$_4$)$_2$SO$_4$ was added to the protamine sulfate-treated extract slowly with stirring over a period of 90 minutes to bring the extract to 50 percent saturation. This was centrifuged at 13,000×g for 20 minutes. The pellet, containing lactate oxidase, was dissolved in 0.1 M potassium phosphate buffer, pH 7, dialyzed against the same buffer, and stored frozen.

2. Assay for Lactate Oxidase

For spectrophotometric assay of the lactate oxidase standard reaction mixtures contained in a total volume of 1.0 ml: 100 μmoles potassium phosphate buffer, pH 7.0, 25 μmoles lactic acid, 30 μg horseradish peroxidase (5.6 purpurogallin units), and 0.25 μmoles orthodianisidine. Samples were equilibrated at 30° C. and then reactions initiated by addition of *S. faecalis* lactate oxidase. Absorbance at 430 nm was measured in a Beckman A-25 Spectrophotometer. Initial rates were calculated from the linear portion of the curve and converted to units of lactate oxidase activity were appropriate. One unit = 1 μmole of dye produced per minute at 30° C. using an $\epsilon = 1.1 \times 10^4$ for orthodianisidine.

Another method to assay for lactate oxidase activity is by means of an oxygen electrode. The following method is illustrative. For the oxygen electrode assay a Yellow Springs Instrument Company Model 53 oxygen electrode apparatus was used; this was equipped with a constant temperature bath and constant speed stirring motor. Routinely, the meter was set at zero percent oxygen with a sample of nitrogen flushed distilled water and at 100% oxygen with a sample of air saturated distilled water. Incubation mixtures which contained in a total volume of 3.0 ml: 280 μmoles potassium phosphate buffer, pH 7.0 and 4.17 μmoles L(+) lactate, were equilibrated at 30°. Reactions were initiated by addition of 0.42 units lactate oxidase and decrease in dissolved oxygen was measured. Control incubations which contained all components except lactate oxidase displayed neither a decrease in dissolved oxygen nor evolution of oxygen upon catalase addition.

3. Methods for Determining Lactic Acid or Lactate a. Lactate dehydrogenase reference method:

A Rapid Lactate STAT-Pack supplied by Calbiochem of Los Angeles, Calif., was used as a source of reagent. Reaction mixtures contained in a total volume of 1.0 ml: 0.22 mmoles tris buffer (pH 9.4), 22 moles glutamate, 2.4 units glutamate pyruvate transaminase, 21 units lactate dehydrogenase, and 3.1 moles NAD+.

Samples were equilibrated at 30° C. and the initial absorbance measured at 340 nm using a Beckman A25 spectrophotometer. Reactions were initiated by addition of either L(+)-lactate standards (6–54 nmoles) or serum (20 μl), and after five minutes the final absorbance was measured at 340 nm. For each serum sample, a blank, which contained serum and 0.9 percent NaCl in a total volume of 1.0 ml, was treated in the same manner as the sample. The $\Delta A_{340}$ for each blank (a correction for serum absorbance at 340 nm) was subtracted from $\Delta A_{340}$ of the appropriate sample, and the lactate concentration of the serum sample was determined by comparison to a lactate standard curve.

b. Lactate oxidase method:

Reaction mixtures contained in a total volume of 1.0 ml: 90 μmoles potassium phosphate buffer, (pH 7.0), 0.2 μmoles orthodianisidine, or 96 μg 4-aminoantipyrene hydrochloride and 32 μg 1,7-dihydroxynaphthalene, 25 μg horseradish peroxidase (5.6-purpurogallin units) and 0.64 mg lactate oxidase (0.4 units).

Samples were equilibrated at 30° C. and the initial absorbance measured at 430 nm. Reactions were initiated by addition of either an L(+)-lactate standard (6–40 nmoles) or serum (20 μl) and after 6 minutes the final absorbance was measured at 430 nm. For each serum sample, a blank, which contained all components except the lactate oxidase, was treated in the same manner as the sample. The $\Delta A_{430}$ for each blank was subtracted from the $\Delta A_{430}$ of the appropriate sample and the lactate concentration was determined by comparison to a lactate standard curve.

EXAMPLE 1

Quantitation of Lactic Acid Using Lactate Oxidase—Solution Assay

Figure 2:
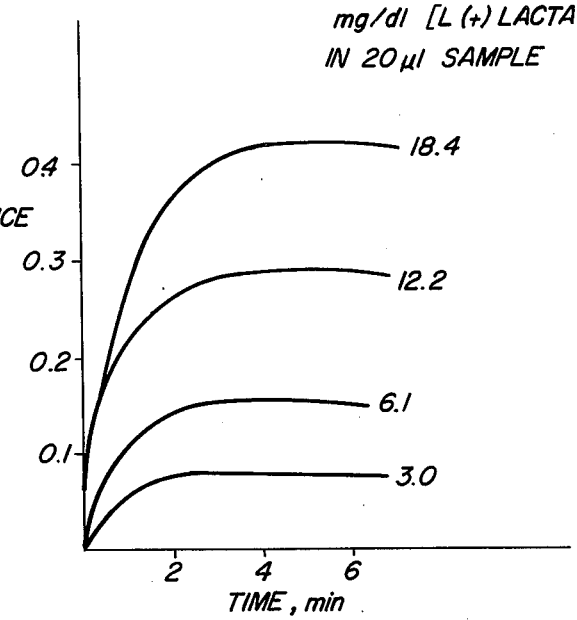

The lactate oxidase obtained from *S. faecalis* was used in the procedure described above for determining lactic acid. The reactions, initiated by the addition of L(+)-lactate at concentrations indicated in FIG. 2, were complete in 6 minutes at 30° C. This rapid reaction in the presence of only 0.4 units of enzyme is due in part to the relatively low $K_m$ (0.20 mM) for L(+)-lactate.

Figure 3:
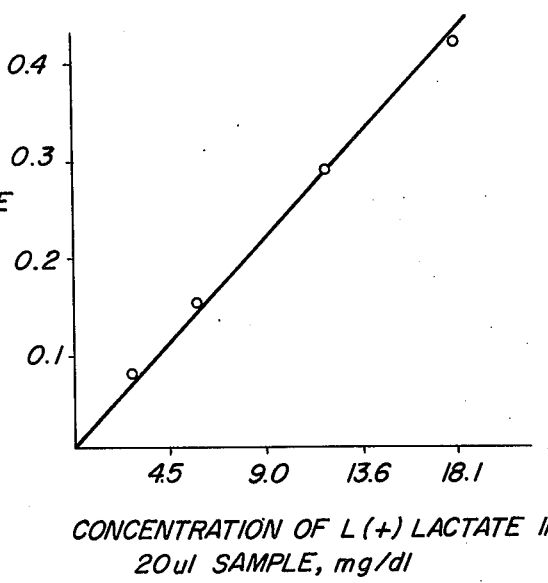

The absorbance (after 6 minutes of reaction) was plotted as a function of the lactic acid concentration as shown in FIG. 3. Dye formation was proportional to the lactic acid concentration over the range tested. This range was equivalent to serum concentrations of 2.97 to 18.6 mg/dl (0.33 mM to 2.03) if one assumes addition of 20 μl of each serum sample to a total volume of 1.0 ml. Normal lactate values of 5 to 15 mg/dl have been reported.

EXAMPLE 2

Comparison of the Lactate Oxidase Method with the Reference Method—Solution Assay Serum samples (20 μl aliquots) were assayed by the reference methods using the procedure described above and the lactate oxidase method using orthodianisidine as the chromogen and then 1,7-dihydroxynaphthalene (DHN) and aminoantipyrene (AAP)-HCl as the color-forming system. The choice of two different color-forming systems demonstrates the latitude of the lactate oxidase method regarding the choice of wavelengths for detection of lactic acid. Results in Table 1 show that there was good correlation between the two methods.

TABLE I

Serum Lactate Quantitation by the Lactate Oxidase Method Compared to the Lactate Dehydrogenase Method

| Serum Sample | Lactate Concentration (mg/dl) | | |
|---|---|---|---|
| | Lactate Dehydrogenase Method | Lactate Oxidase Method | |
| | | DHN/AAP | —O-dianisidine |
| 9 | 10.4 | 9.8 | 7.4 |
| 12 | 17.7 | 14.5 | 15.6 |
| 16 | 13.7 | 12.2 | 9.3 |
| 18 | 14.4 | 15.9 | 13.0 |
| 26 | 20.8 | 21.6 | 17.2 |
| 34 | 8.8 | 8.6 | 7.4 |

EXAMPLE 3

Reproducibility of the Lactic Acid Solution Assay Using the Lactate Oxidase Method The precision of the method of the present invention was determined by repetitive testing of a normal serum sample by means of the method as described above with orthodianisidine color-forming system. From the data in Table II, a coefficient of variation of 2.88 percent was calculated. This compares favorably with the coefficient of variation of 3 percent reported for the lactate dehydrogenase method.

Table II

Reproducibility of the Lactate Oxidase Method for Serum Lactate Quantitation

| | Lactate Concentration mg/dl |
|---|---|
| | 10.772 |
| | 11.500 |
| | 11.515 |
| | 11.909 |
| | 11.500 |
| | 11.909 |
| | 11.681 |
| | 11.531 |
| Mean | 11.551 |
| S.D. ± | 0.336 |
| C.V. % | 2.88 |

The following examples illustrate a preferred embodiment of the invention which uses a multilayer analytical element as illustrated by FIG. 1.

EXAMPLE 4

Multilayer Analytical Element for the Determination of Lactic Acid Using Lactate Oxidase and a Triarylimidazole Dye System A 7 mil Estar support was coated with a reagent layer comprising gelatin (11 g/m²), oleic ether of polyethylene glycol (PEG) (161 mg/m²), Alkanol XC (323 mg/m²), potassium phosphate (807 mg/m²), 5,5-dimethyl-1,3-cyclohexanedione (215 mg/m²), peroxidase (6460 U/m²), lactate oxidase (280 U/m²), bis(vinylsulfonyl methyl)ether (130 mg/m²) and a dispersion of 2(3,5-dimethoxy-4-hydroxyphenyl)-4,5-bis(4-dimethylaminophenyl) imidazole (269 mg/m²) in diethyl lauramide (358 mg/m²); a gel pad layer comprising gelatin (5.4 g/m²), oleic ether of polyethylene glycol (PEG) (161 mg/m²), Alkanol XC (161 mg/m²), potassium phosphate (807 mg/m²), and bis(vinylsulfonylmethyl) ether (65 mg/m²); a subbing layer consisting of poly-n-isopropylacrylamide (320 mg/m²) and a cellulose acetate/TiO₂ spreading layer containing 6 g/m² of cellulose acetate and 46 g/m² of TiO₂.

Figure 4:
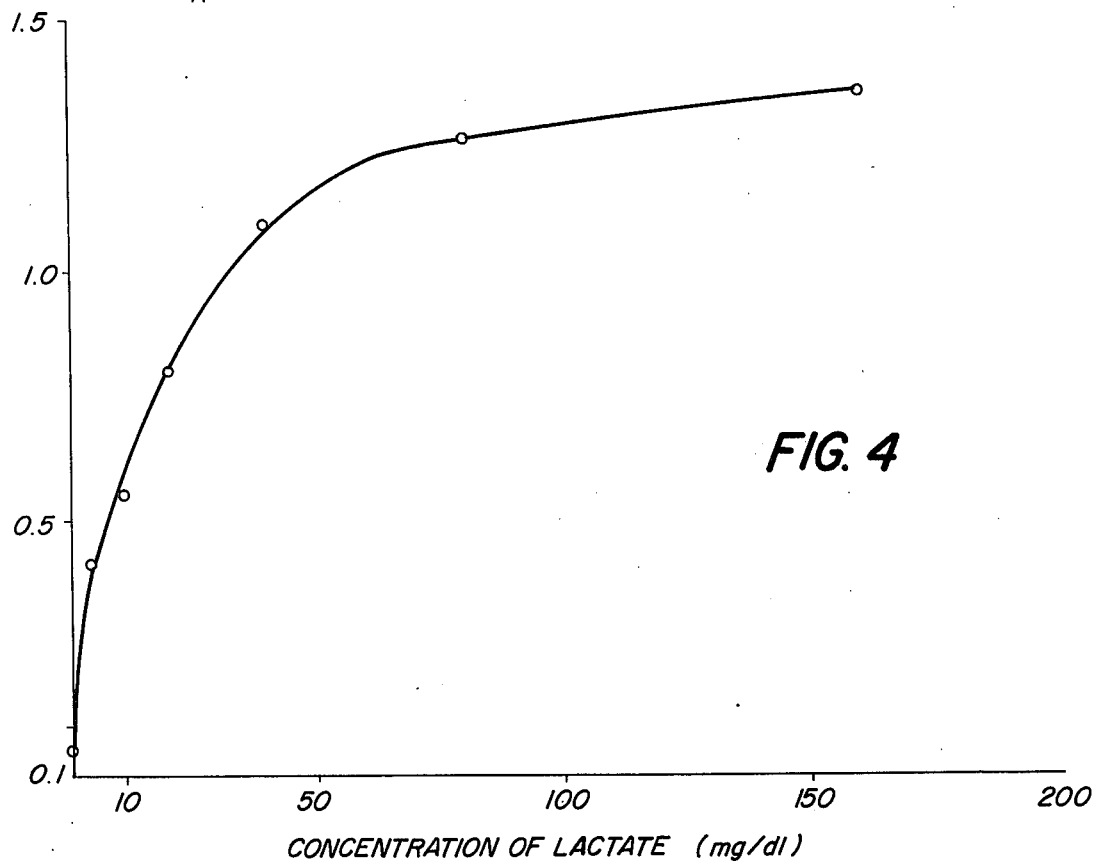

Standards were made by dissolving 6.4 mg/dl lithium lactate in 2.0 ml (33.3 mM) freshly prepared by 7% bovine serum albumin (0.9% of saline added). A plot of the reflection densities versus L-lactate concentration gave the calibration curve shown in FIG. 4.

Serum lactate values were the average of two 10 µl samples applied directly to the web. Density measurements were taken at 10 minutes and lactate concentrations were obtained from the calibration curves.

EXAMPLE 5

Comparison of Lactate Oxidase Method in the Web Format with the Solution Reference Method Serum lactic acid was determined using the analytical element described in Example 4 and also using the solution reference method described above. A plot of the values obtained from two methods, shown in Table III, indicates a 10% bias for the web method. The bias may be introduced in calibration of the web with L-lactate in crystallized and lyophilized bovine serum albumin.

Table III

| Serum Sample | Serum Lactate Values (mg/dl) | |
|---|---|---|
| | Reference Method | Lactate Oxidase Web |
| 9 | 10.4 | 11.3 |
| 12 | 17.5 | 20.2 |
| 16 | 13.5 | 13.2 |
| 18 | 14.3 | 18.6 |
| 21 | 24.3 | 25.3 |
| 26 | 20.6 | 22.8 |
| 34 | 8.8 | 9.9 |

EXAMPLE 6

Reproducibility of the Present Invention Using the Web Format

Two levels of serum lactic acid, 5 and 10 mg/dl, were tested on two separate days to obtain precision data on the coated element embodiment of the present invention. Results are tabulated in Table IV.

Table IV

| | Analytical Variations | |
|---|---|---|
| Number of Assays | 6 | 6 |
| Lactate Level (mg/dl) | 5 | 10 |
| Mean, $D_R$ | 0.844 | 1.360 |
| S.D. ± | .0104 | .0459 |
| C.V. % | 1.2 | 3.4 |

EXAMPLE 7

Multilayer Analytical Element for the Determination of Lactic Acid Using a Self-Coupling Dye System A more readily available chromogen, the 4-isopropoxy-1-naphthol self-coupling dye system, which extended the analytical range of the assay, was used in this element.

The format of the element is that shown in FIG. 1. The layer composition is as follows:

A 7 mil Estar support was coated with a reagent layer comprising gelatin, (16.0 g/m$^2$), sodium phosphate (592 mg/m$^2$), potassium phosphate (356 mg/m$^2$), Triton X-100 (323 mg/m$^2$), 4-isopropoxy-1-naphthol (861 mg/m$^2$), copoly(n-butylmethacrylate-co-styrene-co-2-acrylamido-2-methylpropane sulfonic acid) (55:40:5) (3.4 g/m$^2$), 5,5-dimethyl-1,3-cyclohexanedione (215 mg/m$^2$), peroxidase (118 mg/m$^2$), lactate oxidase (280 U/m$^2$) and bis(vinylsulfonylmethyl)ether (242 mg/m$^2$); a gel pad comprising gelatin (5.4 g/m$^2$), sodium phosphate (140 mg/m$^2$), potassium phosphate (280 mg/m$^2$), Triton X-100 (108 mg/m$^2$) and bis(vinylsulfonylmethyl)ether (81 mg/m$^2$); a subbing layer comprising poly-n-isopropylacrylamide (320 mg/m$^2$) and a cellulose acetate, TiO$_2$ spreading layer of the type described.

Figure 5:
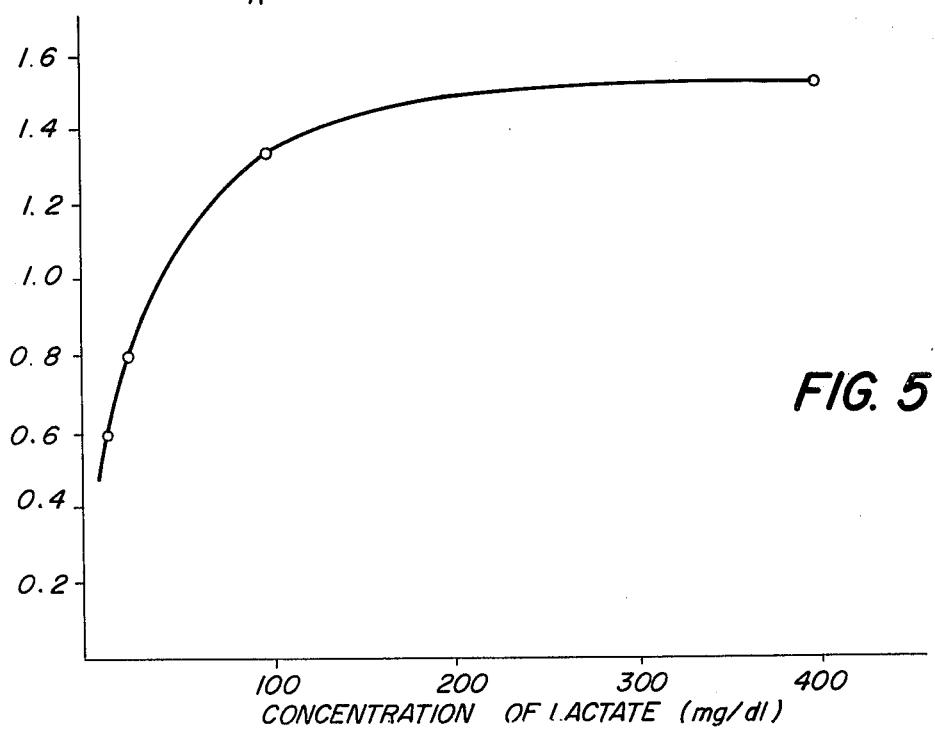

Lactate standards were prepared as previously described, and a calibration curve (FIG. 5) was generated from the concentrations vs density values read at 10 minutes at 37° C.

At 12.5 mg/dl lactate, the standard deviation was (n=9)=0.024, and the coefficient of variation (%) was 4.2

The invention has been described in detail with particular reference to certain preferred embodiments thereof, but it will be understood that variations and modifications can be effeced within the spirit and scope of the invention.

We claim:

1. A composition for the assay of lactic acid or lactate, said composition comprising
    (A) a lactate oxidase which
        (1) is capable of effecting the production of detectable hydrogen peroxide,
        (2) has a specific activity of at least about 0.1µ moles lactate per minute per mg of protein,
        (3) is soluble in water,
        (4) is substantially catalase-free, and
        (5) has a K$_m$ for lactate of at least about 0.2 mM,
    (B) a substance having peroxidative activity, and
    (C) a material that undergoes a detectable change in the presence of hydrogen peroxide and the substance having peroxidative activity.

2. A composition as described in claim 1 wherein the lactate oxidase is obtained from Streptococcus faecalis ATCC 12755.

3. A composition as described in claim 1 wherein the substance having peroxidative activity is a peroxidase.

4. A composition as described in claim 1 wherein the material that undergoes a detectable change is an organic compound tha undergoes a visible change.

5. An element for the detection of lactic acid or lactate, the element comprising a spreading layer and a reagent layer in fluid contact under conditions of use and containing a composition comprising
    (A) a lactate oxidase which
        (1) is capable of effecting the production of detectable hydrogen peroxide,
        (2) has a specific activity of at least about 0.1µ moles lactate per minute per mg of protein,
        (3) is soluble in water,
        (4) is substantially catalase-free, and
        (5) has a K$_m$ for lactate of at least about 0.2 mM,
    (B) a substance having peroxidative activity, and
    (C) a material that undergoes a detectable change in the presence of hydrogen peroxide and the substance having peroxidative activity.

6. An element as described in claim 5 wherein said reagent layer contains said lactate oxidase.

7. An element as described in claim 5 wherein said reagent layer contains a composition comprising a substance having peroxidative activity and a material that undergoes a detectable change in the presence of hydrogen peroxide and said substance having peroxidative activity.

8. An element as described in claim 7 wherein said substance having peroxidative activity is a peroxidase.

9. An element as described in claim 7 wherein the material that undergoes a detectable change is an organic compound that undergoes a visible change.

10. An element as described in claim 5 wherein the lactate oxidase is obtained from *Streptococcus faecalis* ATCC 12755.

11. The element of claim 5 wherein said composition is contained in the reagent layer and further including a third layer, between the spreading layer and the reagent layer, for preventing the material which undergoes a detectable change from migrating into the spreading layer.

12. The element as described in claim 11 which further comprises a support, the reagent layer separating the support from the spreading layer.

13. An element as described in claim 11 wherein said substance having peroxidative activity is a peroxidase.

14. An element as described in claim 11 wherein the material that undergoes a detectable change is an organic compound that undergoes a visible change.

15. An element as described in claim 11 wherein the lactate oxidase is obtained from *Streptococcus faecalis* ATCC 12755.

16. An element for the assay of lactic acid or lactate comprising a spreading layer and a reagent layer in fluid contact under conditions of use and containing a composition comprising
   (A) a lactate oxidase which
      (1) is capable of effecting the production of detectable hydrogen peroxide,
      (2) has a specific activity of at least about 0.1μ moles lactate per minute per mg of protein,
      (3) is soluble in water,
      (4) is substantially catalase-free, and
      (5) has a $K_m$ for lactate of at least about 0.2 mM,
   (B) a substance having peroxidative activity, and
   (C) a material that undergoes a detectable change in the presence of hydrogen peroxide and the substance having peroxidative activity,
said components (B) and (C) being present in the reagent layer, the lactate oxidase being present in a concentration of from about 50 to about 500 (B) being present in a concentration of from about 2000 to about 20,000 U/$m^2$.

17. The element as described in claim 16 wherein said element further comprises a third layer, located between the spreading layer and the reagent layer, for preventing the material that undergoes a detectable change from migrating into the spreading layer.

18. The element as described in claim 17 wherein the material that undergoes a detectable change is a triarylimidazole dye and (B) is present in a concentration of from about 3,000 to about 10,000 U/$m^2$.

19. The element as described in claim 18 wherein the material that undergoes a detectable change is 2(3,5-dimethoxy-4-hydroxyphenyl)-4,5-bis(4-dimethylaminophenyl)imidazole.

20. The element as described in claim 17 wherein the material that undergoes a detectable change is a self-coupling dye and (B) is present in a concentration of from about 3,000 to about 10,000 U/$m^2$.

21. The element as described in claim 20 wherein the material that undergoes a detectable change is 4-isopropoxy-1-naphthol.

22. The element as described in claim 17 which further comprises a support, the reagent layer being nearer to the support than the spreading layer.

23. An element as described in claim 17 wherein the material that undergoes a detectable change is an organic compound that undergoes a visible change.

24. An element as described in claim 17 wherein the lactate oxidase is obtained from *Streptococcus faecalis* ATCC 12755.

25. An element for the detection of lactic acid or lactate comprising a matrix of absorbent material and imbibed therein a composition comprising
   (A) a lactate oxidase which
      (1) is capable of effecting the production of detectable hydrogen peroxide,
      (2) has a specific activity of at least about 0.1μ moles lactate per minute per mg of protein,
      (3) is soluble in water,
      (4) is substantially catalase-free, and
      (5) has a $K_m$ for lactate of at least about 0.2 mM,
   (B) a substance having peroxidative activity, and
   (C) a material that undergoes a detectable change in the presence of hydrogen peroxide and the substance having peroxidative activity.

26. An element as described in claim 25 wherein said lactate oxidase is obtained from *Streptococcus faecalis* ATCC 12755.

27. A method for detecting lactic acid or lactate, said method comprising:
   contacting in an aqueous medium a sample for analysis and a composition comprising
      (A) a lactate oxidase which
         (1) is capable of effecting the production of detectable hydrogen peroxide,
         (2) has a specific activity of at least about 0.1μ moles lactate per minute per mg of protein,
         (3) is soluble in water,
         (4) is substantially catalase-free, and
         (5) has a $K_m$ for lactate of at least about 0.2 mM,
      (B) a substance having peroxidative activity, and
      (C) a material that undergoes a detectable change in the presence of hydrogen peroxide and the substance having peroxidative activity; and p1 detecting said detectable change.

* * * * *